United States Patent [19]

Wadsworth et al.

[11] 4,021,475

[45] May 3, 1977

[54] SYNTHESIS OF ARYL ETHERS OF BIS(HYDROXYMETHYL) ETHER

[75] Inventors: Donald Harold Wadsworth; Richard Sturtevant Vinal, both of Rochester, N.Y.

[73] Assignee: Eastman Kodak Company, Rochester, N.Y.

[22] Filed: Dec. 5, 1975

[21] Appl. No.: 638,009

[52] U.S. Cl. .............................. 260/491; 260/613 R
[51] Int. Cl.² ............................................. C07C 41/00
[58] Field of Search ............ 260/615 A, 613 R, 491

[56] References Cited

UNITED STATES PATENTS

| | | | |
|---|---|---|---|
| 2,246,049 | 6/1941 | Lange | 260/615 A |
| 2,273,786 | 2/1942 | Loder | 260/615 A X |
| 2,446,171 | 8/1948 | Croxall et al. | 260/615 A |
| 2,486,925 | 11/1949 | Carroll | 260/613 |

FOREIGN PATENTS OR APPLICATIONS

| | | | |
|---|---|---|---|
| 1,028,130 | 4/1958 | Germany | |
| 959,162 | 5/1964 | United Kingdom | 260/615 A |

*Primary Examiner*—Bernard Helfin
*Attorney, Agent, or Firm*—Dana M. Schmidt

[57] ABSTRACT

Process for preparing mono- and diaryl ethers of bis(-hydroxymethyl) ether by reaction of the dialkyl esters of polyoxymethylene glycols with phenol or substituted phenol. In a preferred embodiment the reaction is carried out in the presence of a catalyst.

14 Claims, No Drawings

SYNTHESIS OF ARYL ETHERS OF BIS(HYDROXYMETHYL) ETHER

This invention relates to the preparation of aryl ethers of bis(hydroxymethyl) ether by reacting dialkyl esters of polyoxymethylene glycols with phenol. Preferably the reaction is carried out in the presence of a catalyst.

It is known to react phenol with a glycol or a fatty acid having vicinal hydroxy groups according to German Patent No. 1,028,130 issued Apr. 17, 1958. However, no transesteretherification is disclosed.

SUMMARY OF THE INVENTION

According to the process of the invention, aryloxyoxymethylenes or acylaryloxyoxymethylenes are provided by the displacement at elevated temperatures, of acyloxy groups from the several structures RCOO—(C-$H_2O_x$COR by aryloxy and substituted aryloxy groups. X equals 2 or 3. In a preferred embodiment the arylaryloxyoxymethylenes or acylaryloxyoxymethylenes are provided by the displacement at about 170 to 250° C of acyloxy groups by phenoxy and substituted phenoxy groups.

An aliphatic monocarboxylic acid diester having the formula:

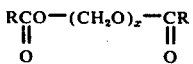

wherein $x$ has the values 2 or 3 and R represents a lower alkyl group of 1 to 4 carbon atoms is reacted with a phenol having the formula:

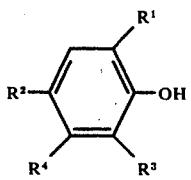

wherein $R^1$, $R^2$, $R^3$ and $R^4$ independently represent hydrogen, halogen such as chloro or bromo, an alkyl group, or a methoxy group; distilling off free monocarboxylic acid (RCOOH) evolved in the reaction.

In one embodiment, a diaryl ether is obtained having the formula:

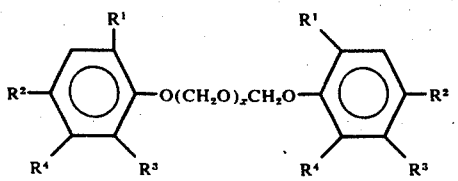

wherein the substituents and $x$ are the same as above.

DETAILED DESCRIPTION OF THE INVENTION

In carrying out the process either with or without a catalyst, the reactants are heated so that the corresponding organic acid (RCOOH) distills at the reaction temperature. The use of various catalysts increases the reaction rates and decreases the reaction temperatures from those observed in corresponding uncatalyzed reactions. Accordingly, operating temperatures substantially lower than those in uncatalyzed reactions minimize undesirable decomposition of reactants and products and extend the scope of the reaction to include use of more volatile starting materials. This reaction permits the use of low-cost and/or easily recoverable catalysts; the direct formation of intermediates which are of a purity sufficient for use without further processing; the formation of valuable, non-toxic intermediates for photographic hardeners; and the formation of intermediates for gelatin hardeners by either a continuous or a batch process.

In a preferred embodiment of the invention, the reaction is carried out at a temperature from about 170° to 190° C in the presence of a non-metallic catalyst. Typically, a stable, inert solvent with a boiling point in the range of 170° to 220° C is used. The oxymethylene glycol diesters useful as starting products are prepared by known procedures from acid anhydrides and formaldehyde oligomers, Angew. Chem. 74, 248 (1962). In the uncatalyzed displacement reaction, organic acid is distilled from a mixture containing the oxymethylene glycol diester and preferably, an excess of the desired phenol. Fifty percent stoichiometric excess of the phenol is particularly useful. The reactants are heated to about 230° to 250° C and stirred while purging with nitrogen to assist agitation and removal of the organic acid (RCOOH) which is distilling from the reaction.

Since the reaction appears to be equilibrium controlled, it is desirable to assist in removing the acid which is distilling from the reaction. This removal can be assisted by using an inert solvent which boils at the reaction temperature and carries the acid with it as it volatilizes. In a preferred embodiment, nitrogen purging or an inert solvent having a boiling point at about 175°–200° C is used. Heating is continued at the reaction temperature until the rate of distillation drops off, generally from 1 to 4 hours. Usually the residual reaction mixture is cooled to about 100° to 150° C and then poured into a non-solvent to precipitate the product, after which the product is isolated. The uncatalyzed thermal process of the invention is, of course, limited to starting materials and products that are not subject to decomposition at the elevated temperatures employed. Useful ethers for the uncatalyzed process include bis(acetoxymethyl) ether, bis(trichloroacetoxymethyl) ether, bis(iso-butyryloxymethyl) ether, and bis(acetoxymethoxy) methane. Typical phenols include p-methoxyphenol, p-bromophenol, 2,4-dichlorophenol, 2,4,6-trichlorophenol, p-phenylphenol, and p-butylphenol, etc.

A catalyzed displacement reaction can be run at considerably lower temperatures, usually from about 170° to 190° C, preferably from about 175° to 185° C. The particular solvents which may be used in those situations where solvents are desirable include any solvents in which the reactants are miscible and which do not react with the reactants. Solvents which may be used include o-dichlorobenzene, 1,2,4-trichlorobenzene, etc.

Non solvents which are useful in isolating the desired products of the process include those which do not react with the final product such as ethanol, isopropanol, petroleum ether, cyclohexane, etc.

Preferred non-metallic catalysts are compounds containing metal ions in their higher normal oxidation states. These preferred catalysts may be soluble or insoluble in the reaction medium. The metal ions do not contain outer d-electrons, but these metal ions are known to form relatively strong bonds with oxygen atoms and organic functional groups, such as esters or ethers. The classification of catalysts as metallic and non-metallic is described on page 3 of "Heterogeneous Catalysis" by S. J. Thomson and G. Webb, John Wiley and Sons, Inc., N.Y., 1968.

Preferred catalysts include zinc acetate, zinc oxide, aluminum alkoxide, aluminum acetylacetonate, aluminum oxide, aluminum sulfate, zirconyl sulfate, zinc phthalocyanine and zirconium oxynitrate, silica-alumina mixes, and molecular sieves. Other catalysts that can be employed include $Zr(OCOCH_3)_4$, $BF_3 \cdot (C_2H_5)_3N$, zirconium (IV) ammonium sulfate, $NH_4HSO_4$, $CoSO_4$, $MgSO_4$, zinc acetylacetonate, $CuBr_2$(anhydrous), $Sm_2O_3$, $ZrO$(acetylacetonate)$_2$, and $CoWO_4$. These compounds generally fall in the class of non-metallic catalysts of metal ions known to form relatively strong bonds with oxygen atoms in organic ligands.

However, any catalyst may be used provided it demonstrates catalytic activity as determined by the following screening procedure:

A solution of 3.0 g (0.015 mole) of 2,4,6-trichlorophenol and 0.80 g (0.005 mole) of bis(acetoxymethyl) ether in 7.5 ml of o-dichlorobenzene containing 0.05 - 0.10 g of the material to be screened as a catalyst is heated at reflux for 30 minutes in an open flask. A sample is examined by vapor phase chromatography for the presence of α-acetoxy-α'-2, 4,6-trichlorophenoxymethyl ether. All materials which produce more product than the same reactants without the material are judged to be catalysts.

Many of the catalysts may be heterogeneous in their active form. Other examples, such as aluminum stearate may provide improved homogeneous catalysts of increased selectivity and reaction rate.

A wide range of phenols can be employed in this embodiment of the invention, including the compounds useful in the uncatalyzed process: for example, phenol, o- and p-chlorophenol, cresol, 2,4-dichlorophenol and xylenol.

Typical solvents include o-dichlorobenzene, 1,2,4-trichlorobenzene cis-decalin, ligroine (b.p. 170°–200° C), p-cymene, and n-undecane. Products are generally isolated by precipitation from a non-solvent in sufficient purity to be used without further purification.

The following examples are included for a further understanding of the invention.

EXAMPLE 1

Bis(2,4,6-trichlorophenoxymethyl) Ether

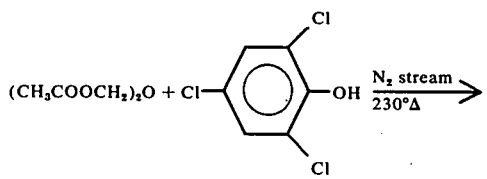

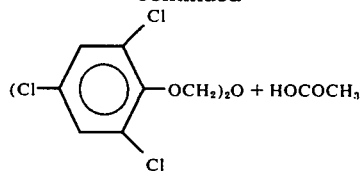

A solution of 81.0 g (0.50 mole) of bis(acetoxymethyl) ether in 591 g (3.0 moles) of trichlorophenol was heated with stirring and nitrogen purging to 230° C. The nitrogen flow was adjusted to a rate sufficient to cause steady distillation of acetic acid without excessive loss of trichlorophenol. After 4.25 hours, the reaction mixture was cooled to 130° C, poured into ethanol and filtered to furnish 150.5 g of product (73% yield) mp 179°–181° C.

EXAMPLE 2

Bis(2,4,6-trichlorophenoxymethyl) Ether

A solution of 16.2 g (0.10 mole) of bis(acetoxymethyl) ether and 59.0 g (0.30 mole) of 2,4,6-trichlorophenol in 75 ml of o-dichlorobenzene was treated with an appropriate catalyst (see Table I) and heated until slow distillation resulted (pot temperature, 180°–200 C). Distillate was removed at 180°–200° C at a rate of 10–15 ml/hr for 2–4 hrs. The solution was cooled to 130°–150° C and poured into isopropanol. The desired product was isolated by filtration.

TABLE I

| Catalyst | Amount(g) | Product(g) | Yield % |
|---|---|---|---|
| $Al_2O_3$ | 2 | 39 | 89 |
| $Al_2O_3 \cdot SiO_2$ | 2 | 19 | 43 |
| $Al_2(SO_4)_3 \cdot xH_2O$ | 1 | 34 | 77 |
| $Zn(OCOCH_3)_2$ | 0.5 | 32 | 73 |
| ZnO | 0.5 | 37 | 73 |
| $Al[OCH(CH_3)_2]_3$ | 0.5 | 32.5 | 74 |
| Molecular Sieves* | 2 | 26 | 60 |

*Zeolites having an open network structure used to separate hydrocarbons and other mixtures by selective occlusion of one or more of the constituents.

EXAMPLE 3

Bis(2-Chlorophenoxymethyl) Ether

A solution of 16.2 g (0.10 mole) of bis(acetoxymethyl) ether in 75 ml o-chlorophenol was treated with 2.0 g of neutral aluminum oxide (80–240 mesh) and heated sufficiently to cause slow distillation (pot temp. 180°–185° C). After collecting approximately 40 ml of distillate over a 3 hr. period, the reaction mixture was filtered hot and stripped of all volatile material in vacuo. The oily residue was crystallized from methanol to furnish 23.6 g of product, mp 62.5°–3° 79% yield. The above reaction will not occur at a significant rate without catalyst because of the low boiling point of o-chlorophenol (175°–176° C).

EXAMPLE 4

Bis(p-chlorophenoxymethyl) Ether

A solution of 16.2 g (0.1 mole) of bis(acetoxymethyl) ether and 39 g (0.30 mole) of p-chlorophenol in 80 ml of o-dichlorobenzene were treated with 1.0 g of neutral aluminum oxide (80–240 mesh) and heated to reflux (pot temp. 180°–185° C). Distillate was removed at about 10 ml/hr over a 4 hour period. The reaction mixture was filtered hot, stripped in vacuo,

EXAMPLE 5

Bis(2,4,6-trichlorophenoxymethyl) Ether

A solution of 19.2 g of bis(acetoxymethoxy)methane and 59.0 g of 2,4,6-trichlorophenol in 75 ml o-dichlorobenzene was heated (pot temp. 180°–185° C) with 2.0 g of alumina (⅛ in pellets) and subjected to slow distillation (10 ml/hr) for 4 hours. The reaction mixture was cooled to 140° C and poured into isopropanol to furnish 37.5 g of product, mp 179°–181° C; 86% yield.

EXAMPLE 6

Bis(p-methoxyphenylmethyl) Ether

A solution of 16.2 g (0.10 mole) of bis(acetoxymethyl) ether and 37.0 g (0.30 mole) of p-methoxyphenol in 80 ml of o-dichlorobenzene containing 2.0 g of ⅛ in alumina pellets was heated to reflux (pot temp. 180°–185° C). Distillate was removed at a rate of 10 ml/hr for 4 hours. The reaction mixture was cooled to about 20° C and poured into 500 ml of cyclohexane. The resulting oily layer was separated and triturated with a second 100 ml portion of warm cyclohexane. The combined triturates were washed with cold sodium hydroxide solution to remove the remaining phenol and evaporated to dryness. The oily residue (6.6 g) was crystallized from cyclohexane-petroleum ether (30°–60° C) to furnish 5.0 g (19% yield) of product, mp 58°–59° C.

EXAMPLE 7

α-Acetoxy-α'-(2,4,6-trichlorophenoxy)methyl Ether

A solution of 16.2 g (0.10 mole) of bis(acetoxymethyl) ether and 9.9 g (0.05 mole) of 2,4,6-trichlorophenol in 80 ml of o-dichlorobenzene was stirred and heated (pot temp. 180°–185° C) with 2.0 g of ⅛ in alumina pellets. Distillate was collected at a rate of about 10 ml/hr for 4 hours, the reaction mixture cooled, and poured into methanol. After filtration of the bis(2,4,6-trichlorophenoxymethyl) ether by-product, the solvent was evporated in vacuo and the residue recystallized to furnish 7.9 g (26.4% yield) of product, mp 79°–82° C.

EXAMPLE 8

Formation of Bis(2,4,6-trichlorophenoxymethyl) Ether in a Hot Tube Reactor

A solution of 162.0 g (1.0 mole) of bis(acetoxymethyl) ether and 590.0 g (3.0 mole) of 2,4,6-trichlorophenol in 800 ml of 1,2,4-trichlorobenzene was passed down through a heated tube. The furnace temperature was 220°–240° C and the take-off temperature was initially 90° C and reached a maximum of 180° C. Product was collected by filtering the solution cooled to about 20° C after each pass. After eight passes (contact time about 1 to 2 minutes per pass) a total of 232 g (53% yield) of product had been collected.

The invention has been described in detail with particular reference to preferred embodiments thereof, but it will be understood that variations and modifications can be effected within the spirit and scope of the invention.

What is claimed is:

1. A process of preparing an arylaryloxyoxymethylene or an acylaryloxyoxymethylene comprising heating a mixture of an ester having the formula:

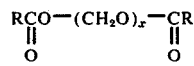

wherein $x$ has the values 2 or 3 and R represents a lower alkyl group of 1 to 4 carbon atoms and a phenol having the formula:

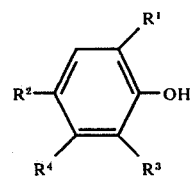

wherein $R_1$, $R_2$, $R_3$ and $R_4$ are each independently H, halogen, methoxy, phenyl and alkyl having 1 to 18 carbon atoms, to at least the boiling point of free monocarboxylic acid having the formula RCOOH, at which temperature the ester and phenol react to form said arylaryloxyoxymethylene or acylaryloxyoxymethylene and RCOOH and removing said RCOOH from said mixture.

2. A process of claim 1 in which said ester is reacted with said phenol at about 170° to about 250° c.

3. A process of claim 1 which comprises an additional step of cooling the reaction mixture to about 100° to 150° C and pouring the cooled mixture into a non-solvent to precipitate the product and isolating the product.

4. A process of claim 1 in which the said ester is reacted with about 1 to about 50 molar equivalents of said phenol.

5. A process of claim 1 in which R is $CH_3$.

6. A process of claim 1 in which $R^1$ is halogen and $R^2$, $R^3$ and $R^4$ *are each H.*

7. A process of claim 1 in which $R^1$ and $R^2$ are each halogen and $R^3$ *and $R^4$ are each H.*

8. A process of claim 1 in which $R^1$, $R^2$ and $R^3$ each is halogen and $R^4$ is H.

9. A process of claim 1 in which R is $CH_3$ and $x$ is 2.

10. A process of claim 1 in which R is $CH_3$ and $x$ is 3.

11. A process of claim 1 in which $R^2$ is methoxy and $R^1$, $R^3$ and $R^4$ are each H.

12. A process of claim 1 in which a solvent is used which does not react with the reactants.

13. A process of claim 1, wherein said heating step is carried out in the presence of a catalyst which incorporates metal ions known to form relatively strong bonds with oxygen atoms in organic ligands.

14. A process of claim 1, wherein said heating step is carried out in the presence of a catalyst selected from the group consisting of zinc acetate, zinc oxide, aluminum alkoxide, aluminum acetylacetonate, aluminum oxide, aluminum sulfate, zirconyl sulfate, zinc phthalocyanine, zirconium oxynitrate, silica-alumina mixes, molecular sieves, $Zr(OCHOCH_3)_4$, $BF_3 \cdot (C_2H_5)_3N$, zirconium (IV) ammonium sulfate, $NH_4HSO_4$, $CoSO_4$, $MgSO_4$, zinc acetylacetonate, $CuBr_2$(anhydrous), $Sm_2O_3$, $ZrO$(acetylacetonate)$_2$, and $CoWO_4$.